(12) United States Patent
Xu et al.

(10) Patent No.: US 8,748,661 B2
(45) Date of Patent: Jun. 10, 2014

(54) POLYAMINO POLYKETIDE ANTIBIOTICS AND USES THEREOF

(75) Inventors: Jinling Xu, Singapore (SG); Lianhui Zhang, legal representative, Singapore (SG); Jien Wu, Singapore (SG); Haibao Zhang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 269 days.

(21) Appl. No.: 13/128,220

(22) PCT Filed: Nov. 9, 2009

(86) PCT No.: PCT/SG2009/000414
§ 371 (c)(1),
(2), (4) Date: Sep. 23, 2011

(87) PCT Pub. No.: WO2010/053455
PCT Pub. Date: May 14, 2010

(65) Prior Publication Data
US 2013/0022553 A1    Jan. 24, 2013

Related U.S. Application Data

(60) Provisional application No. 61/112,280, filed on Nov. 7, 2008.

(51) Int. Cl.
*C07C 233/36* (2006.01)
*C07C 211/13* (2006.01)
*A61K 31/16* (2006.01)
*A61K 31/164* (2006.01)
*C12P 13/00* (2006.01)
*C12P 13/02* (2006.01)

(52) U.S. Cl.
USPC ........... 564/197; 564/512; 514/613; 514/626; 435/128; 435/129

(58) Field of Classification Search
None
See application file for complete search history.

(56) References Cited

FOREIGN PATENT DOCUMENTS

CN          1245164 A       2/2000
WO     WO 03/039529 A1     5/2003

OTHER PUBLICATIONS

Database CAPLUS on STN, Acc. No. 2000:752195, CN1245164 A (Feb. 23, 2000) (abstract and structures).*
Costerton et al., "Microbial Biofilms," *Annu. Rev. Microbiol.* 49:711-745, 1995.
Costerton et al., "Bacterial Biofilms: A Common Cause of Persistent Infections," *Science* 284:1318-1322, 1999.
Govan et al., "Microbial Pathogenesis in Cystic Fibrosis: Mucoid *Pseudomonas aeruginosa* and *Burkholderia cepacia*," *Microbiological Reviews* 60(3):539-574, 1996.
Lewis, "Riddle of Biofilm Resistance," *Antimicrobial Agents and Chemotherapy* 45(4):999-1007, 2001.
Liu et al., "Chemical Structure Determination of Echcin I, a New Antibiotic Produced by Erwinia Chrysanthemi," *Journal of China Pharmaceutical University* 1996-09. (Abstract).
Samson et al., "Transfer of *Pectobacterium chrysanthemi* (Burkholder et al. 1953) Brenner et al. 1973 and *Brenneria paradisiaca* to the genus *Dickeya* gen. nov. as *Dickeya chrysanthemi* comb. nov. and *Dickeya paradisiaca* comb. nov. and delineation of four novel species, *Dickeya dadantii* sp. nov., *Dickeya dianthicola* sp. nov., *Dickeya dieffenbachiae* sp. nov. and *Dickeya zeae* sp. nov.," *International Journal of Systematic and Evolutionary Microbiology* 55:1415-1427, 2005.
Seo et al., "Characterization of an antibacterial substance produced by *Erwinia carotovora* subp. *carotovora* Ecc 32," *J. Gen. Plant. Pathol.* 70:273-277, 2004.
Stickler et al., "Biofilms on Indwelling Urethral Catheters Produce Quorum-Sensing Signal Molecules In Situ and In Vitro," *Applied and Environmental Microbiology* 64(9):3486-3490, 1998.
Wu et al., "$^{13}$C Labeling reveals multiple amination reactions in the biosynthesis of a novel polyketide polyamine antibiotic zeamine from *Dickeya zeae*," *Chem. Commun.* 46:333-335, 2010.
Zhang et al., "Factors affecting biosynthesis by *Xanthomonas albilineans* of albicidin antibiotics and phytotoxins," *Journal of Applied Microbiology* 85:1023-1028, 1998.
An et al., "The Impact and Molecular Genetics of Bacterial Biofilms," in Wen-Tso Liu et al. (eds.), *Environmental Molecular Microbiology*, Caister Academic Press, 2010, pp. 211-226.
Nicolaus, "Symbiotic Approach to Drug Design," *Decision Making in Drug Research*, Raven Press, New York, 1983, pp. 173-186.

* cited by examiner

*Primary Examiner* — Brian J Davis
(74) *Attorney, Agent, or Firm* — Seed IP Law Group PLLC

(57) ABSTRACT

The present invention relates to novel polyamino polyketide antibiotics, methods of their production as well as methods of using these antibiotics, for example, for inhibition or removal of biofilm formation or for treating bacterial infection with these antibiotics.

18 Claims, 2 Drawing Sheets

POLYAMINO POLYKETIDE ANTIBIOTICS AND USES THEREOF

CROSS REFERENCE TO RELATED APPLICATIONS

Figure 1:
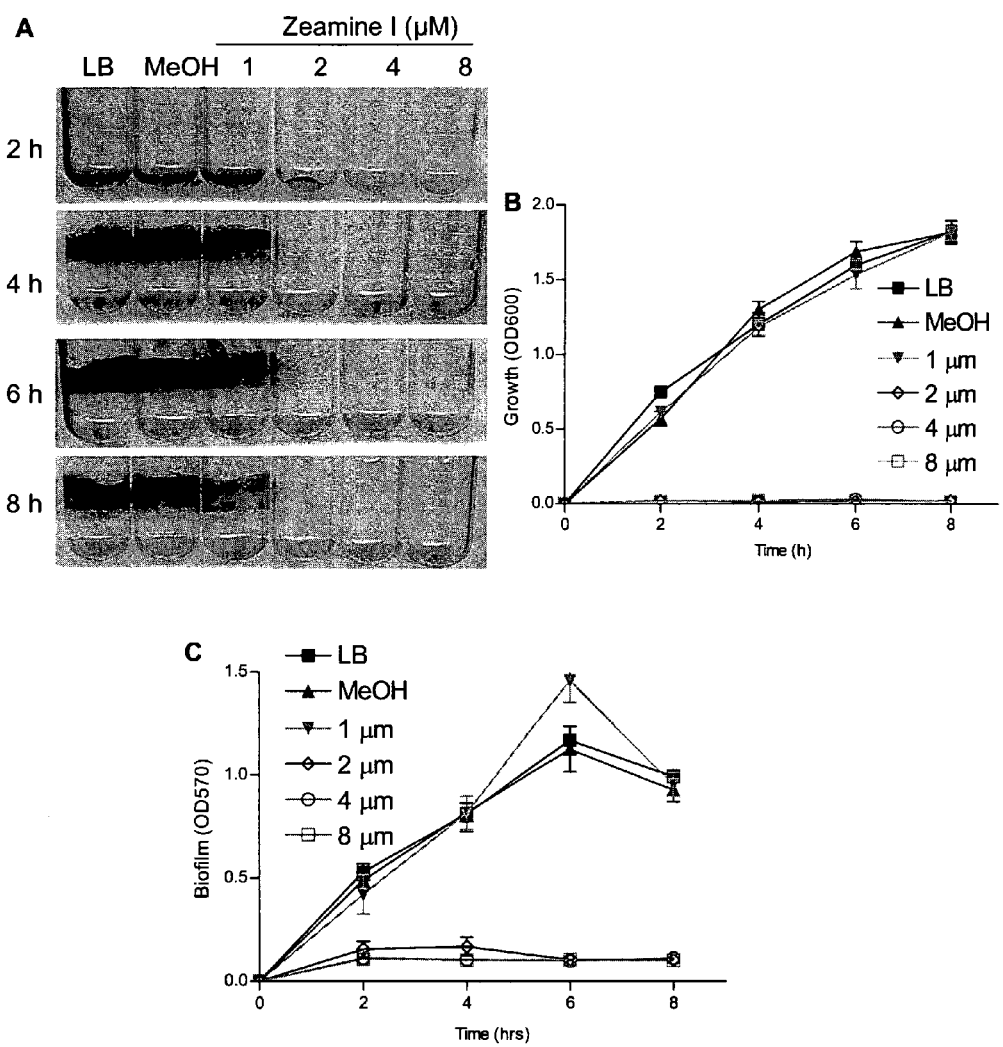

This application makes reference to and claims the benefit of priority of an application for "Polyamino polyketide antibiotics and method of manufacturing thereof and method of treating bacterial infections" filed on Nov. 7, 2008 with the United States Patent and Trademark Office, and there duly assigned U.S. Provisional Ser. No. 61/112,280. The contents of said application filed on Nov. 7, 2008 is incorporated herein by reference for all purposes, including an incorporation of any element or part of the description, claims or drawings not contained herein.

FIELD OF THE INVENTION

The present invention relates to novel polyamino polyketide antibiotics, methods of their production as well as methods for treating bacterial infection and removal of bacterial biofilms or inhibition of biofilm formation with these antibiotics.

BACKGROUND OF THE INVENTION

Discovery of antibiotics and their subsequent clinical application world wide represent one of the landmark advances of modern medicine. However, emergence of super-bugs that are resistant to multidrugs has become a critical public and health concern. Antibiotic-resistant bacterial infections are becoming more and more common in clinical and nosocomial settings. As a Darwinian consequence of antibiotic usage, selection of antibiotic resistance is an inevitable. Identification of new antibiotics and development of new treatments are therefore of critical importance for the control and prevention of microbial infections.

SUMMARY OF THE INVENTION

In a first aspect, the present invention relates to compounds of formula I

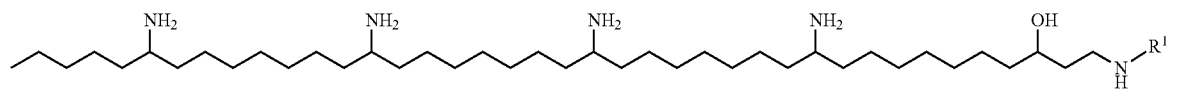

Formula I wherein $R^1$ is hydrogen, unsubstituted or substituted $C_1$-$C_{10}$ alkyl, unsubstituted or substituted $C_1$-$C_{10}$ alkenyl, unsubstituted or substituted $C_1$-$C_{10}$ alkynyl, unsubstituted or substituted $C_3$-$C_8$ cycloalkyl, unsubstituted or substituted $C_1$-$C_{10}$ alkoxy, unsubstituted or substituted $C_3$-$C_8$ cycloalkoxy, unsubstituted or substituted $C_6$-$C_{14}$ aryl, an unsubstituted or substituted 5- to 10-membered heteroaryl wherein 1 to 4 ring atoms are independently selected from nitrogen, oxygen or sulfur, an unsubstituted or substituted 5- to 10-membered heteroalicyclic ring wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, and —S(O)$_2$NRR', R and R' are independently selected from the group consisting of hydrogen and unsubstituted or substituted $C_1$-$C_{10}$ alkyl, unsubstituted or substituted $C_1$-$C_{10}$ alkenyl, unsubstituted or substituted $C_1$-$C_{10}$ alkynyl;

or a tautomer, geometrical isomer, enantiomer, diastereomer, racemate form, pharmaceutically acceptable salt or prodrug thereof.

In another aspect, the present invention relates to compositions comprising the compounds of the invention.

In a further aspect, the invention is directed to the compounds of the invention for use as a medicament, such as an anti-bacterial agent or antibiotic.

In another embodiment, the invention also relates to the use of one or more of the invented compounds for the treatment or prevention of a bacterial infection in a subject.

In still another aspect, the invention is directed to a method of treating a bacterial infection in a subject comprising administering a therapeutically effective amount of one or more of the compound of the invention to a subject in need thereof.

In still another aspect, the invention is directed to the use of a compound or a composition of the invention for the removal/treatment of a biofilm or for inhibiting biofilm formation.

In another embodiment, the invention also encompasses a method for producing a compound of the invention comprising (a) cultivating an organism of the genus *Dickeya*; and (b) isolating said compound from said organism.

In one of these embodiments, the organism of the genus *Dickeya* is the species *Dickeya zeae*. In a still further aspect, the invention relates to a *Dickeya zeae* DZ1 strain or a mutant thereof producing any of the compounds of the invention. The strain DZ1 has been deposited with the American Type Culture Collection (ATCC) under the accession number PTA-10319.

In another aspect, the invention also relates to polyamino polyketid compounds which are obtainable by isolation from *Dickeya zeae*. These compounds may have an anti-bacterial effect. In one specific embodiment, the *Dickeya zeae* used for the isolation of these compounds is *Dickeya zeae* strain DZ1 or a mutant thereof.

DETAILED DESCRIPTION OF THE INVENTION

Definitions

Unless otherwise stated the following terms used in the specification and claims have the meanings discussed below:

The term "*Dickeya*" is used in accordance with its general meaning to refer to the genus "*Dickeya*" (taxon identifier 204037) that belongs to the family of Enterobacteriaceae (classification according to http://www.uniprot.org/taxonomy/204037) and that is a known pythopathogenic organism that causes soft rot in plants such as rice. The term "*Dickeya zeae*" refers to the species of the genus *Dickeya* that is known in the art too and has been given the taxon identifier 204042 (classification according to http://www.uniprot.org/ taxonomy/204042). (see also Samson et al, Transfer of *Pectobacterium chrysanthemi* (Burkholder et al. 1953) Brenner et al. 1973 and *Brenneria paradisiaca* to the genus *Dickeya* gen. nov. as *Dickeya chrysanthemi* comb. nov. and *Dickeya paradisiaca* comb. nov. and delineation of four novel species, *Dickeya dadantii* sp. nov., *Dickeya dianthicola* sp. nov., *Dickeya dieffenbachiae* sp. nov. and *Dickeya zeae* sp. nov. Int. Journal of Systematic and Evolutionary Microbiology (2005) July; 55 (Pt 4):1415-27). Other examples of suitable species of the genus *Dickeya* that can be used in the present invention include *Dickeya dadantii, Dickeya dieffenbachiae, Dickeya paradisiacal, Dickeya* sp. 2187, to mention only a few.

The term "mutant" when used in connection with the strain DZ1 (ATCC accession number PTA-10319) refers to a variant of the parental strain as well as methods for obtaining a mutant or variant in which the desired biological activity, i.e. the production of one or more compounds of formula (I) is similar or identical to that of the parental strain. The "parent strain" as defined herein is the original DZ1 strain before mutagenesis. Mutants may occur in nature without the intervention of man. They also are obtainable by treatment with or by a variety of methods and compositions known to those of skill in the art. For example, the strain DZ1 may be treated with a chemical such as N-methyl-N'-nitro-N-nitrosoguanidine, ethylmethanesulfone, or by irradiation using gamma, x-ray, or UV-irradiation, or by other means well known to those practiced in the art. A mutant strain or variant of DZ1 can also be obtained by directed genetic engineering, for example, by overexpression or deletion of the genes encoding relevant enzymes or proteins. The mutants may be obtained to improve the yield of a compound of formula (I) or to cause the production of a modified compound of formula (I), meaning a compound of formula (I) that is different from the compound of formula (I) produced by the parental strain DZ1. All such mutants and genetically engineered variants derived from the parental strain DZ1 are also encompassed by the present invention.

"Alkyl" refers to a saturated aliphatic hydrocarbon including straight chain, or branched chain groups. Preferably, the alkyl group has 1 to 10 carbon atoms (whenever a numerical range; e.g., "1-10", is stated herein, it means that the group, in this case the alkyl group, may contain 1 carbon atom, 2 carbon atoms, 3 carbon atoms, etc. up to and including 10 carbon atoms). More specifically, it may be a medium size alkyl having 1 to 6 carbon atoms or a lower alkyl having 1 to 4 carbon atoms e.g., methyl, ethyl, n-propyl, isopropyl, butyl, iso-butyl, tert-butyl and the like. The alkyl group may be substituted or unsubstituted. When substituted, the substituent group(s) is one or more, for example one two, three, four or five groups, individually selected from the group consisting of $C_3$-$C_8$ cycloalkyl, $C_6$-$C_{14}$ aryl, 5-10 membered heteroaryl wherein 1 to 4 ring atoms are independently selected from nitrogen, oxygen or sulfur, 5-10 membered heteroalicyclic wherein 1 to 3 ring atoms are independently nitrogen, oxygen or sulfur, hydroxy, $C_1$-$C_{10}$ alkoxy, $C_3$-$C_8$ cycloalkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, sulfinyl, sulfonyl, amino, and —$NR^{10}R^{11}$ where $R^{10}$ and $R^{11}$ are independently selected from the group consisting of hydrogen, $C_1$-$C_4$ alkyl, $C_3$-$C_8$ cycloalkyl, $C_6$-$C_{14}$ aryl, carbonyl, acetyl, sulfonyl, amino, and trifluoromethanesulfonyl, or $R^{10}$ and $R^{11}$, together with the nitrogen atom to which they are attached, combine to form a five-or six-membered heteroalicyclic ring.

A "cycloalkyl" group refers to an all-carbon monocyclic ring (i.e., rings which share an adjacent pair of carbon atoms) of 3 to 8 ring atoms wherein one of more of the rings does not have a completely conjugated pi-electron system e.g., cyclopropyl, cyclobutyl, cyclopentyl, cyclohexyl, cyclobutenyl, cyclopentenyl, cyclohexenyl, and the like. Examples, without limitation, of cycloalkyl groups are cyclopropane, cyclobutane, cyclopentane, cyclopentene, cyclohexane, adamantane, cyclohexadiene, cycloheptane and, cycloheptatriene. A cycloalkyl group may be substituted or unsubstituted. When substituted, the substituent group(s) is one or more, for example one or two groups, individually selected from $C_1$-$C_{10}$ alkyl, $C_3$-$C_8$ cycloalkyl, $C_6$-$C_{14}$ aryl, 5-10 membered heteroaryl wherein 1 to 4 ring atoms are independently selected from nitrogen, oxygen or sulfur, 5-10 membered heteroalicyclic wherein 1 to 3 ring atoms are independently nitrogen, oxygen or sulfur, hydroxy, $C_1$-$C_{10}$ alkoxy, $C_3$-$C_8$ cycloalkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, sulfinyl, sulfonyl, amino, and —$NR^{10}R^{11}$, with $R^{10}$ and $R^{11}$ as defined above.

An "alkenyl" group refers to an alkyl group, as defined herein, consisting of at least two carbon atoms and at least one carbon-carbon double bond e.g., ethenyl, propenyl, butenyl or pentenyl and their structural isomeric forms such as 1-or 2-propenyl, 1-, 2-, or 3-butenyl and the like.

An "alkynyl" group refers to an alkyl group, as defined herein, consisting of at least two carbon atoms and at least one carbon-carbon triple bond e.g., acetylene, ethynyl, propynyl, butynyl, or pentynyl and their structural isomeric forms as described above.

An "aryl" group refers to an all-carbon monocyclic or fused-ring polycyclic (i.e., rings which share adjacent pairs of carbon atoms) groups of 6 to 14 ring atoms and having a completely conjugated pi-electron system. Examples, without limitation, of aryl groups are phenyl, naphthalenyl and anthracenyl. The aryl group may be substituted or unsubstituted. When substituted, the substituted group(s) is one or more, for example one, two, or three substituents, independently selected from the group consisting of $C_1$-$C_{10}$ alkyl, $C_3$-$C_8$ cycloalkyl, $C_6$-$C_{14}$ aryl, 5-10 membered heteroaryl wherein 1 to 4 ring atoms are independently selected from nitrogen, oxygen or sulfur, 5-10 membered heteroalicyclic wherein 1 to 3 ring atoms are independently nitrogen, oxygen or sulfur, hydroxy, $C_1$-$C_{10}$ alkoxy, $C_3$-$C_8$ cycloalkoxy, aryloxy, mercapto, alkylthio, arylthio, cyano, halo, trihalomethyl, carbonyl, thiocarbonyl, O-carbamyl, N-carbamyl, O-thiocarbamyl, N-thiocarbamyl, C-amido, N-amido, C-carboxy, O-carboxy, nitro, silyl, sulfinyl, sulfonyl, amino, and —$NR^{10}R^{11}$ with $R^{10}$ and $R^{11}$ as defined above. Preferably the substituent(s) is/are independently selected from chloro, fluoro, bromo, methyl, ethyl, hydroxy, methoxy, nitro, carboxy, methoxycarbonyl, sulfonyl, or amino.

A "heteroaryl" group refers to a monocyclic or fused aromatic ring (i.e., rings which share an adjacent pair of atoms) of 5 to 10 ring atoms in which one, two, three or four ring atoms are selected from the group consisting of nitrogen, oxygen and sulfur and the rest being carbon. Examples, without limitation, of heteroaryl groups are pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, isobenzofuryl, benzothienyl, benzotriazolyl, isobenzothienyl, indolyl, isoindolyl, 3H-indolyl, benzimidazolyl, benzothiazolyl, benzoxazolyl, quinolizinyl, quinazolinyl, pthalazinyl, quinoxalinyl, cinnnolinyl, napthyridinyl, quinolyl, isoquinolyl, tetrazolyl, 5,6,7,8-tetrahydroquinolyl, 5,6,7,8- tetra-hydroisoquinolyl, purinyl, pteridinyl, pyridinyl, pyrimidinyl, carbazolyl, xanthenyl or benzoquinolyl. The heteroaryl group may be substituted or unsubstituted. When substituted, the substituted group(s) is one or more, for example one or two substituents, independently selected from the group consisting of $C_1$-$C_{10}$ alkyl, $C_3$-$C_8$ cycloalkyl, $C_6$-$C_{14}$ aryl, 5-10 membered heteroaryl wherein 1 to 4 ring atoms are independently selected from nitrogen, oxygen or sulfur, 5-10 membered heteroalicyclic wherein 1 to 3 ring atoms are independently nitrogen, oxygen or sulfur, hydroxy, $C_1$-$C_{10}$ alkoxy, $C_3$-$C_8$ cycloalkoxy, aryloxy, mercapto, alkylthio, arylthio, cyano, halo, trihalomethyl, carbonyl, thiocarbonyl, O-carbamyl, N-carbamyl, O-thiocarbamyl, N-thiocarbamyl, C-amido, N-amido, C-carboxy, O-carboxy, nitro, silyl, sulfinyl, sulfonyl, amino, and —$NR^{10}R^{11}$, with $R^{10}$ and $R^{11}$ as defined above. Preferably the substituent(s) is/are independently selected from chloro, fluoro, bromo, methyl, ethyl, hydroxy, methoxy, nitro, carboxy, methoxycarbonyl, sulfonyl, or amino.

A "heteroalicyclic" group refers to a monocyclic or fused ring of 5 to 10 ring atoms containing one, two, or three heteroatoms in the ring which are selected from the group consisting of nitrogen, oxygen and —$S(O)_n$ where n is 0-2, the remaining ring atoms being carbon. The rings may also have one or more double bonds. However, the rings do not have a completely conjugated pi-electron system. Examples, without limitation, of heteroalicyclic groups are pyrrolidine, piperidine, piperazine, morpholine, imidazolidine, tetrahydropyridazine, tetrahydrofuran, thiomorpholine, tetrahydropyridine, and the like. The heteroalicyclic ring may be substituted or unsubstituted. When substituted, the substituted group(s) is one or more, for example one, two, or three substituents, independently selected from the group consisting of $C_1$-$C_{10}$ alkyl, $C_3$-$C_8$ cycloalkyl, $C_6$-$C_{14}$ aryl, 5-10 membered heteroaryl wherein 1 to 4 ring atoms are independently selected from nitrogen, oxygen or sulfur, 5-10 membered heteroalicyclic wherein 1 to 3 ring atoms are independently nitrogen, oxygen or sulfur, hydroxy, $C_1$-$C_{10}$ alkoxy, $C_3$-$C_8$ cycloalkoxy, aryloxy, mercapto, alkylthio, arylthio, cyano, halo, trihalomethyl, carbonyl, thiocarbonyl, O-carbamyl, N-carbamyl, O-thiocarbamyl, N-thiocarbamyl, C-amido, N-amido, C-carboxy, O-carboxy, nitro, silyl, sulfinyl, sulfonyl, amino, and —$NR^{10}R^{11}$, with $R^{10}$ and $R^{11}$ as defined above. The substituent(s) is/are for example independently selected from chloro, fluoro, bromo, methyl, ethyl, hydroxy, methoxy, nitro, carboxy, methoxycarbonyl, sulfonyl, or amino.

A "hydroxy" group refers to an —OH group.

An "alkoxy" group refers to an —O-unsubstituted alkyl and —O-substituted alkyl group, as defined herein. Examples include and are not limited to methoxy, ethoxy, propoxy, butoxy, and the like.

A "cycloalkoxy" group refers to an —O-cycloalkyl group, as defined herein. One example is cyclopropyloxy.

An "aryloxy" group refers to both an —O-aryl and an —O-heteroaryl group, as defined herein. Examples include and are not limited to phenoxy, napthyloxy, pyridyloxy, furanyloxy, and the like.

A "mercapto" group refers to an —SH group.

An "alkylthio" group refers to both an S-alkyl and an —S-cycloalkyl group, as defined herein. Examples include and are not limited to methylthio, ethylthio, and the like.

An "arylthio" group refers to both an —S-aryl and an —S-heteroaryl group, as defined herein. Examples include and are not limited to phenylthio, napthylthio, pyridylthio, furanylthio, and the like.

A "sulfinyl" group refers to a —S(O)—R" group, wherein, R" is selected from the group consisting of hydrogen, hydroxy, alkyl, cycloalkyl, aryl, heteroaryl (bonded through a ring carbon) and heteroalicyclic (bonded through a ring carbon), as defined herein.

A "sulfonyl" group refers to a —$S(O)_2R"$ group wherein, R" is selected from the group consisting of hydrogen, hydroxy, alkyl, cycloalkyl, aryl, heteroaryl (bonded through a ring carbon) and heteroalicyclic (bonded through a ring carbon), as defined herein.

A "trihalomethyl" group refers to a —$CX_3$ group wherein X is a halo group as defined herein e.g., trifluoromethyl, trichloromethyl, tribromomethyl, dichlorofluoromethyl, and the like.

"Carbonyl" refers to a —C(═O)—R" group, where R" is selected from the group consisting of hydrogen, alkyl, cycloalkyl, aryl, heteroaryl (bonded through a ring carbon) and heteroalicyclic (bonded through a ring carbon), as defined herein. Representative examples include and the not limited to acetyl, propionyl, benzoyl, formyl, cyclopropylcarbonyl, pyridinylcarbonyl, pyrrolidin-lylcarbonyl, and the like.

A "thiocarbonyl" group refers to a —C(═S)—R" group, with R" as defined herein.

"C-carboxy" and "carboxy" which are used interchangeably herein refer to a —C(═O)O—R" group, with R" as defined herein, e.g. —COOH, methoxycarbonyl, ethoxycarbonyl, benzyloxycarbonyl, and the like.

An "O-carboxy" group refers to a —OC(═O)R" group, with R" as defined herein, e.g. methylcarbonyloxy, phenylcarbonyloxy, benzylcarbonyloxy, and the like.

An "acetyl" group refers to a —C(═O)$CH_3$ group.

A "carboxylic acid" group refers to a C-carboxy group in which R" is hydrogen.

A "halo" or "halogen" group refers to fluorine, chlorine, bromine or iodine.

A "cyano" group refers to a —CN group.

A "nitro" group refers to a —$NO_2$ group.

An "O-carbamyl" group refers to a —OC(═O)$NR^{10}R^{11}$ group, with $R^{10}$ and $R^{11}$ as defined herein.

An "N-carbamyl" group refers to a $R^{11}$OC(═O)$NR^{10}$— group, with $R^{10}$ and $R^{11}$ as defined herein.

An "O-thiocarbamyl" group refers to a —OC(═S)$NR^{10}R^{11}$ group, with $R^{10}$ and $R^{11}$ as defined herein.

An "N-thiocarbamyl" group refers to a $R^{11}$OC(═S)$NR^{10}$— group, with $R^{10}$ and $R^{11}$ as defined herein.

An "amino" group refers to an —$NR^{10}R^{11}$ group, wherein $R^{10}$ and $R^{11}$ are independently hydrogen or unsubstituted lower alkyl, e.g., —$NH_2$, dimethylamino, diethylamino, ethylamino, methylamino, and the like.

A "C-amido" group refers to a —C(═O)$NR^{10}R^{11}$ group, with $R^{10}$ and $R^{11}$ as defined herein. For example, $R^{10}$ is hydrogen or unsubstituted $C_1$-$C_4$ alkyl and $R^{11}$ is hydrogen, $C_1$-$C_4$ alkyl optionally substituted with heteroalicyclic, hydroxy, or amino. For example, C(═O)$NR^{10}R^{11}$ may be aminocarbonyl, dimethylaminocarbonyl, diethylaminocarbonyl, diethyl amino ethylaminocarbonyl, ethylaminoethylaminocarbonyl, and the like.

An "N-amido" group refers to a $R^{11}$C(═O)$NR^{10}$— group, with $R^{10}$ and $R^{11}$ as defined herein, e.g. acetylamino, and the like.

A "pharmaceutical composition" refers to a mixture of one or more of the compounds described herein, or physiologically/pharmaceutically acceptable salts or prodrugs thereof, with other chemical components, such as physiologically/pharmaceutically acceptable carriers and excipients. The purpose of a pharmaceutical composition is to facilitate administration of a compound to an organism.

The compound of Formula I may also act as a prodrug. A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but then is metabolically hydrolyzed to the carboxylic acid, the active entity, once inside the cell where water solubility is beneficial. A prodrug may be converted into the parent drug by various mechanisms, including enzymatic processes and metabolic hydrolysis.

A further example of a prodrug might be a short polypeptide, for example, without limitation, a 2-10 amino acid polypeptide, bonded through a terminal amino group to a carboxy group of a compound of this invention wherein the polypeptide is hydrolyzed or metabolized in vivo to release the active molecule. The prodrugs of compounds of Formula I are within the scope of this invention.

Additionally, it is contemplated that compounds of Formula I would be metabolized by enzymes in the body of the organism such as a human being to generate a metabolite that has an antibiotic or anti-microbial effect. Such metabolites are within the scope of the present invention.

As used herein, a "physiologically/pharmaceutically acceptable carrier" refers to a carrier or diluent that does not cause significant irritation to an organism and does not abrogate the biological activity and properties of the administered compound.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatine, vegetable oils and polyethylene glycols.

As used herein, the term "pharmaceutically acceptable salt" refers to those salts which retain the biological effectiveness and properties of the parent compound. Such salts include, but are not restricted to: (1) an acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, such as sodium or potassium, an alkaline earth ion, such as magnesium or calcium, or an aluminum ion; or coordinates with an organic base such as ethanolamine, diethanolamine, triethanolamine, tromethamine, N-methylglucamine, and the like.

The term "antibiotic" or "anti-bacterial agent" relates to a compound that inhibits, abrogates or prevents the growth of microbes, such as bacteria.

"Bacterial infection" relates to an infection of an organism with microbes or bacteria, for example pathogenic bacteria. The bacteria may, for example, be selected from the genus *Acinetobacter, Actinomyces, Aeromonas, Bordetella, Borrelia, Brucella, Burkholderia, Campylobacter, Chlamydia, Clostridium, Corynebacterium, Enterococcus, Erwinia, Escherichia, Francisella, Haemophilus, Helicobacter, Klebsiella, Legionella, Leptospira, Listeria, Mycobacterium, Mycoplasma, Neisseria, Pseudomonas, Rickettsia, Salmonella, Shigella, Staphylococcus, Streptococccus, Treponema, Veillonella, Vibrio* or *Yersinia*. Specific examples of pathogenic bacteria are *Staphylococcus aureus, Mycobacterium smegmatis, Pseudomonas aeruginosa, Burkholderia cepacia, Klebsiella pneumonia, Aeromonas hydrophila, Erwinia carotovora, Erwinia chrysanthemi*, or *Escherichia coli*.

"Treat", "treating" and "treatment" refer to a method of alleviating or abrogating a bacterial infection and/or its attendant symptoms.

"Prevent", "preventing" and "prevention" refer to a method of hindering a bacterial infection from occurring, i.e. a prophylactic method.

"Subject" refers to a living organism, for example a mammal, including a human being.

"Therapeutically effective amount" refers to that amount of the compound being administered which will relieve to some extent one or more of the symptoms of the disease/infection being treated.

Illustrative Embodiments

The present invention is based on the inventor's surprising finding that isolates from strains belonging to the species of *Dickeya zeae* and the genus *Dickeya* produce bactericidal compounds against bacterial pathogens.

Compounds

The bactericidal compounds are typically compounds of formula I

Formula I $$\text{NH}_2 \quad \text{NH}_2 \quad \text{NH}_2 \quad \text{NH}_2 \quad \text{OH}$$

structure with R¹ on terminal NH group wherein $R^1$ is hydrogen, unsubstituted or substituted $C_1$-$C_{10}$ alkyl, unsubstituted or substituted $C_1$-$C_{10}$ alkenyl, unsubstituted or substituted $C_1$-$C_{10}$ alkynyl, unsubstituted or substituted $C_3$-$C_8$ cycloalkyl, unsubstituted or substituted $C_1$-$C_{10}$ alkoxy, unsubstituted or substituted $C_3$-$C_8$ cycloalkoxy, unsubstituted or substituted $C_6$-$C_{14}$ aryl, an unsubstituted or substituted 5- to 10-membered heteroaryl wherein 1 to 4 ring atoms are independently selected from nitrogen, oxygen or sulfur, an unsubstituted or substituted 5- to 10-membered heteroalicyclic ring wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, and —S(O)$_2$NRR', R and R' are independently selected from the group consisting of hydrogen and unsubstituted or substituted $C_1$-$C_{10}$ alkyl, unsubstituted or substituted $C_1$-$C_{10}$ alkenyl, unsubstituted or substituted $C_1$-$C_{10}$ alkynyl;

or a tautomer, geometrical isomer, enantiomer, diastereomer, racemate form, pharmaceutically acceptable salt or prodrug thereof.

In specific embodiments of the invented compounds, $R^1$ is hydrogen or —C(O)R and R is unsubstituted or substituted $C_1$-$C_{10}$ alkyl, for example substituted heptanyl, such as 3-amino-4,6-dihydroxy-2-methyl-heptan-7-yl.

In a specific embodiment, the invented compound has formula II (also referred herein as Zeamine I) or formula III (also referred herein as Zeamine II)

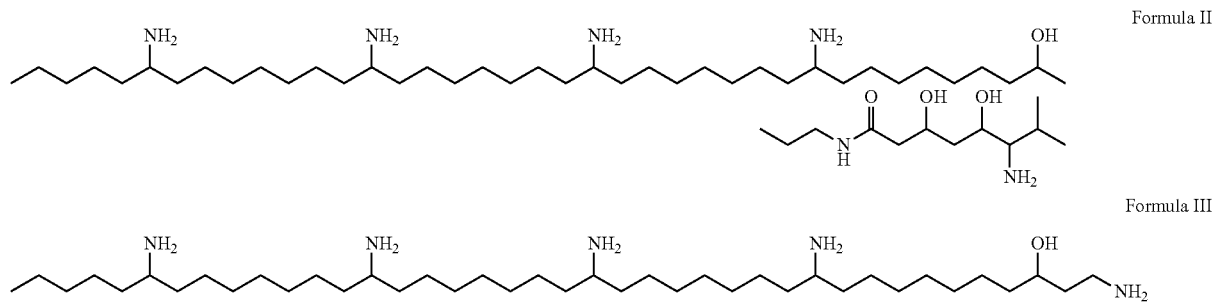

Formula II

Formula III

Utility

In one embodiment of the invention, the invented compounds are used in a method for the treatment or prevention of a bacterial infection in a subject or organism. The bacterial infection may be caused by a Gram negative or a Gram positive bacterium. The bacterial infection may, for example, be caused by bacteria of the genus *Acinetobacter, Actinomyces, Aeromonas, Bordetella, Borrelia, Brucella, Burkholderia, Campylobacter, Chlamydia, Clostridium, Corynebacterium, Enterococcus, Erwinia, Escherichia, Francisella, Haemophilus, Helicobacter, Klebsiella, Legionella, Leptospira, Listeria, Mycobacterium, Mycoplasma, Neisseria, Pseudomonas, Rickettsia, Salmonella, Shigella, Staphylococcus, Streptococccus, Treponema, Veillonella, Vibrio* or *Yersinia*. In one particular embodiment, the infection is caused by *Staphylococcus aureus, Mycobacterium smegmatis, Pseudomonas aeruginosa, Burkholderia cepacia, Klebsiella pneumonia, Aeromonas hydrophila, Erwinia carotovora, Erwinia chrysanthemi*, or *Escherichia coli*. The subject affected by the bacterial infection may be a mammal, such as a human being.

In another embodiment the invention is directed to the use of a compound or a composition of the invention for the removal/treatment of a biofilm or for inhibiting biofilm formation.

In this context it is noted that a wide variety of microorganisms, including both Gram-negative and Gram-positive bacteria, form and exist as biofilms under various conditions (Costerton et al., 1999; Sutherland, 2001). A biofilm is a complex aggregation of microbial cells marked by excretion of a protective and adhesive matrix. In most cases, a biofilm is recognized as a surface attached community with microbial cells interconnected by an extracellular matrix of polymeric substances, but occasionally non-attached or loosely attached bacterial cell aggregates can also be observed. Biofilm development can be divided into several key steps including attachment, microcolony formation, biofilm maturation and dispersion; and in each step bacteria may recruit different components and molecules including flagella, type IV pili, DNA and exopolysaccharides. Biofilm-forming bacteria pose severe problems in environment, industry and healthcare sectors due to increased bacterial survival competence in the environment and the protective nature of biofilms that prevents effective eradication. For example, bacterial biofilm associated chronic infections, and the medical device- and ship-associated biofilms are serious healthcare or industry problems (Costerton et al., 1999; O'Toole et al., 2000b; Donlan and Costerton, 2002; Parsek and Singh, 2003; see also An S. et al (2010), The Impact and Molecular Genetics of Bacterial Biofilms pages 212 to 226 in, Environmental Molecular Microbiology, Caister Academic Press, ISBN 978-1-904455-52-3).

In this context, it is noted that the term "biofilm or biofilms" are defined herein in accordance with its regular meaning in the art as an association of microorganisms growing attached to a surface and producing a slime layer of extracellular polymers in which the microbial consortia is embedded in a protective environment (for a review see: Costerton et al., Ann. Rev. Microbiol. 49: 711-45, 1995, An S et al, supra or see also International patent application WO 2003/039529). Biofilms represent a severe problem as bacteria integrated in such a polymer matrix develop resistance to conventional antimicrobial agents. *P. aeruginosa* cells, for example, growing in an alginate slime matrix have been demonstrated to be resistant to antibiotics (e.g., aminoglycosides, P-lactam antibiotics, fluoroquinolones) and disinfectants (Govan & Deretic, Microbiol. Rev. 60: 539-74, 1996). Several mechanisms for biofilm-mediated resistance development have been proposed (Costerton et al., Science 284: 1318-22, 1999).

In most natural, clinical and industrial settings bacteria are predominantly found in biofilms. Drinking water pipes, ship hulls, teeth or medical devices represent typical surfaces colonized by bacteria. On the one hand biofilms decrease the life time of materials through corrosive action in the industrial field, a process also referred to as "biofouling". On the other hand two thirds of all bacterial infections in humans are associated with biofilms (Lewis, Antimicrob. Agents Chemother. 45: 999-1007, 2001). *Pseudomonas aeruginosa*, for example, forms infectious biofilms on surfaces as diverse as cystic fibrosis lung tissue, contact lenses, and catheter tubes (Stickler et al., Appl. Environm. Microbiol. 64: 3486-90, 1998). Thus, inhibition of biofilm formation of *P. aeruginosa* results in an impaired ability to form biofilms and therefore in an increased susceptability to antibacterial treatment.

In line with the above, the compounds of the present invention can, for example, be applied to bacteria listed under the first paragraph of Utility above. In the following it is explained that the compounds of the present invention can be used as antibacterial agents in various applications.

In a first embodiment, the compounds are useful for the treatment of mammalian in particular human diseases caused by bacteria through the inhibition of bacterial growth and interference of bacterial physiology. Such diseases include endocarditis, respiratory and pulmonary infections (preferably in immunocompromized and cystic fibrosis patients), bacteremia, central nervous system infections, ear infections including external otitis, eye infections, bone and joint infections, urinary tract infections, gastrointestinal infections and skin and soft tissue infections including wound infections, pyoderma and dermatitis which all can be triggered by *Pseudomonas aeruginosa*, for example. Furthermore, the compounds can, for example, also be used for the treatment of pulmonary infections caused by *Burkholderia cepacia* (preferably in immunocompromized and cystic fibrosis patients), gastroenteritis and wound infections caused by *Aeromonas lçydrophila*, sepsis in tropical and subtropical areas caused by *Chrofnobacterium violaceum*, diarrhoea with blood and haemolytic uremic syndrome (HUS) caused by *Escherichia coli*, yersiniosis triggered by *Yersinia enterocolitica* and *Y. pseudotuberculosis*, and transfusion-related sepsis and fistulous pyoderma caused by *Serratia liquefaciens*, to name only a few.

The compounds of the invention can also be used to prevent and/or treat plant diseases, where inhibition of bacterial growth and interference and bacterial physiology reduces or abolishes virulence of bacterial plant pathogens. Such diseases include crown gall tumors caused by *Agrobacterium tumefaciens*, soft rot caused by *Burkholderia cepacia, Erwinia carotovora* and *Erwinia chrysanthemi*, sweet corn and maize infections caused by *Pantoea stewartii* and wilt disease caused by *Katstonia solanacearum*.

In another embodiment, the compounds can be used for the prevention and/or treatment of animal diseases, for example, fish diseases such as septicemia caused by *Aeromonas hydrophila* and *Vibrio anguillarum*, furunculosis in salmonids caused by *Aeromonas salmonicida*, prawn infections caused by *Vibrio harveyi* and enteric redmouth disease caused by *Yersinia ruckeri*, but also for the prevention and/or treatment of insect diseases caused, for example, by *Xenorhabdus nematophilus*.

The present invention also provides a method for reducing the virulence of bacterial pathogens employing, for example, but not limited to, an AHL-based signaling system. In one embodiment, a method is provided to remove, diminish, detach or disperse a bacterial biofilm from a living or nonliving surface by treating the surface with a compound of Formula (I). This method is also useful to prevent biofilm formation on a living or nonliving surface by treating the surface with a compound of Formula (I) before bacterial colonization can initialize. The term "biofilm" refers to cell aggregations comprising either a single type of organism or a mixture of more than one organism. It the latter case, these films are referred to as "mixed biofilms". It is clear to persons skilled in the art, that the compounds of the present invention can be applied in a wide variety of different fields such as environmental, industrial and medical applications in order to prevent and/or treat damages or diseases caused by bacteria.

In one aspect, the compounds of Formula (I) can be used for all kinds of surfaces in private and public areas, where it is beneficial to interfere Gram-negative or Gram-positive bacteria in order to prevent and/or treat colonization and biofilm formation. A compound of Formula (I) can be applied to the surface as a solution of the compound, alone or together with other materials such as conventional surfactants, preferably sodium dodecyl sulfate, or detergents, biocides, fungicides, antibiotics, pH regulators, perfumes, dyes or colorants. In combination with a bacteriocidal agent, e.g., the compounds of Formula (I) inhibit virulence or biofilm formation whilst the bacteriocidal agent kills the pathogens.

In one embodiment, the compounds can be used as antibacterial agent for topical use in cleaning and treatment solutions such as disinfectants, detergents, household cleaner and washing powder formulations in the form of a spray or a dispensable liquid. In one embodiment these solutions can be applied to windows, floors, clothes, kitchen and bathroom surfaces and other surfaces in the area of food preparation and personal hygiene.

In addition, the compounds of Formula (I) can be used as antibacterial ingredients in personal hygiene articles, toiletries and cosmetics. An example of such toiletries can include oral hygiene products. An oral hygiene product refers to any composition which is used in the mouth in order to promote oral hygiene. These compositions may be in the form of aqueous solutions, as in a mouthwash composition, gels, as in toothpaste or dentrifice compositions, solids, as in lozenges, or combined with fillers, as in chewing gum compositions. In this context, a dentrice refers to a paste, liquid or powder used to help maintain acceptable oral hygiene. Exemplary personal hygiene articles include but are not limited to soaps, shampoos, shower gels, ointments, creams, lotions, deodorants and disinfectants and storage solutions for contact lenses. Examples of cosmetics include make-up, eye liner, lip stick, lip gloss to mention only a few. Therefore, in one embodiment, the present invention relates to a composition as described above, comprising the compounds of formula (I).

In another embodiment, the compounds can be used to prevent or treat bacterial biofilms in industrial settings such as ship hulls, paper manufacturing, oil recovery and food processing. The compounds can also be applied to water processing plants or drinking water distribution systems where the colonized surface (for example by *Pseudomonas aeruginosa*) may be the inside of an aqueous liquid system such as water pipes, water injection jets, heat exchangers and cooling towers. Until now biocides are the preferred tools to encounter these problems, but since biocides do not have a high specificity for bacteria, they are often toxic to humans as well. This can be circumvented by the application of a compound of the present invention.

In a further embodiment, the present invention relates to a method of inhibiting and/or preventing medical device-associated bacterial infections. The invention, provides articles coated and/or impregnated with a compound of Formula (I) in order to inhibit and/or prevent biofilm formation thereon. The articles may be surgical instruments, blood bag systems or medical devices such as either permanently implanted devices such as artificial heart valves, prosthetic joints, voice prosthesis, stents, shunts or not permanently implanted devices such as endotracheal or gastrointestinal tubes, pacemakers, surgical pins or indwelling catheters. Examples of indwelling catheters are urinary catheters, vascular catheters, peritoneal dialysis catheter, central venous catheters and needle-less connectors. The catheter materials can be polyvinylchloride, polyethylene, latex, Teflon®, polyurethane and silicone, a mixture thereof, or similar polymeric materials.

In this context it is noted that in order to reduce the risk of catheter-related bacterial infections, several catheters coated and/or impregnated with antiseptic or antimicrobial agents such as chlorhexidine/silver-sulfadiazine and minocycline/rifampin, respectively, have been developed. Furthermore, collection bags or layers sandwiched between an external surface sheath and a luminal silicone sheath have been constructed to overcome rapid loss of antimicrobial activity. Nevertheless, the emerging risk of bacterial resistance against traditional antibiotics limits the routine use of antibiotic-coated catheters.

The compounds of the present invention, however, offer the possibility to effectively reduce catheter-related bacterial infections with a low risk of resistance development due to a novel therapeutic strategy targeting highly sensitive signal transduction mechanisms in bacteria. One form of application is the coating and/or impregnating of catheter materials on both the inner and outer catheter surfaces. The compounds of Formula (I) may also be included in a mixture of antibacterial agents released continuously from a catheter-associated depot into the environment.

Administration and Pharmaceutical Compositions

A compound of the present invention or a pharmaceutically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

As used herein, "administer" or "administration" refers to the delivery of a compound of Formula (I) or a pharmaceutically acceptable salt thereof or of a pharmaceutical composition containing a compound of Formula (I) or a pharmaceutically acceptable salt thereof of this invention to an organism for the purpose of prevention or treatment of a bacterial infection.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration are oral and parenteral.

Alternatively, one may administer the compound in a local rather than systemic manner, for example, via injection of the compound directly into a vessel, optionally in a depot or sustained release formulation.

Pharmaceutical compositions of the present invention may be manufactured by processes well known in the art, e.g., by means of conventional mixing, dissolving, granulating, drageemaking, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatine, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatine, as well as soft, sealed capsules made of gelatine and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound.

Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextrane. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD: D5W) consists of VPD diluted 1:1 with a 5% dextrose in water solution. This cosolvent system dissolves hydrophobic compounds well, and itself produces low toxicity upon systemic administration.

Naturally, the proportions of such a co-solvent system may be varied considerably without destroying its solubility and toxicity characteristics. Furthermore, the identity of the co-solvent components may be varied: for example, other low toxicity nonpolar surfactants may be used instead of Polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for stabilization may be employed.

The pharmaceutical compositions herein also may comprise suitable solid or gel phase carriers or excipients. Examples of such carriers or excipients include, but are not limited to, calcium carbonate, calcium phosphate, various sugars, starch, cellulose derivatives, gelatine, and polymers such as polyethylene glycols.

Many of the compounds of the invention may be provided as physiologically acceptable salts wherein the claimed compound may form the negatively or the positively charged species. Examples of salts in which the compound forms the positively charged moiety include, without limitation, the sodium, potassium, calcium and magnesium salts formed by the reaction of a carboxylic acid or sulfonic acid group in the compound with an appropriate base (e.g. sodium hydroxide (NaOH), potassium hydroxide (KOH), Calcium hydroxide ($Ca(OH)_2$), etc.).

Pharmaceutical compositions suitable for use in the present invention include compositions wherein the active ingredients are contained in an amount sufficient to achieve the intended purpose, e.g., the treatment of a bacterial infection.

More specifically, a therapeutically effective amount means an amount of compound effective to prevent, alleviate or ameliorate symptoms of bacterial infection or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from the described assays. Then, the dosage can be formulated for use in animal models so as to achieve a circulating concentration range that includes the MIC as determined in the experiments (i.e., the minimum concentration of the test compound which achieves inhibition of bacterial growth). Such information can then be used to more accurately determine useful doses in humans.

Toxicity and therapeutic efficacy of the compounds described herein can be determined by standard pharmaceutical procedures in cell cultures or experimental animals, e.g., by determining the MIC and the $LD_{50}$ for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition.

Dosage amount and interval may be adjusted individually to provide plasma levels of the active species which are sufficient to maintain the anti-bacterial effect. These plasma levels are referred to as minimal effective concentrations (MECs).

Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%.

In cases of local administration or selective uptake, the effective local concentration of the drug may not be related to plasma concentration and other procedures known in the art may be employed to determine the correct dosage amount and interval.

The amount of a composition administered may, of course, be dependent on the subject being treated, the severity of the affliction, the manner of administration, the judgment of the prescribing physician, etc.

The compositions may, if desired, be presented in a pack or dispenser device, such as a kit approved by a regulatory authority, such as EMEA or FDA, which may contain one or more unit dosage forms containing the active ingredient. The pack may for example comprise metal or plastic foil, such as a blister pack. The pack or dispenser device may be accompanied by instructions for administration.

The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration.

Compositions comprising a compound of the invention formulated in a compatible pharmaceutical carrier may also be prepared, placed in an appropriate container, and labeled for treatment of an indicated condition.

Production

In another aspect, the invention relates to methods for producing a compound of the invention. These methods can comprise the steps of cultivating *Dickeya zeae* (or another suitable species of the genus *Dickeya*) and isolating said compound from *Dickeya zeae*. In certain embodiments, the cultivating step may comprise incubation of *Dickeya zeae* in a yeast extract broth or minimal medium. The yeast broth may comprise Bacto tryptone, yeast extract, sucrose, NaCl, agar and/or magnesium sulfate. The minimal medium may comprise potassium phosphate, sodium sulfate, mannitol, glycerol, magnesium sulfate, ferrous sulfate, calcium chloride, and/or manganese chloride and may have a pH of 7.0. The cultivating step may be carried out for 24 hours and/or at 28° C.

The isolation of the compounds of the invention from the cultivated *Dickeya zeae* may comprise separation of the supernatant from the cells by centrifugation, basification of the supernatant, concentration of the supernatant by rotary evaporation, extraction of the supernatant by organic solvent, such as a n-butanol:ethylacetate mixture (2:1), gel filtration chromatography of the extract, and/or reverse phase HPLC, such as reverse phase gradient HPLC.

In one embodiment of the inventive method, *Dickeya zeae* is *Dickeya zeae* strain DZ1 (ATCC accession number PTA-10319) or a mutant thereof.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

BRIEF DESCRIPTION OF THE DRAWINGS

In order to better understand the present invention and to demonstrate how it may be carried out in practice, illustrative embodiments will now be described by way of non-limiting examples only, with reference to the accompanying drawings, in which:

FIG. 1 shows the influence of zeamine I on biofilm formation by *Pseudomonas aeruginosa* PAO1. FIG. 1A shows the influence of zeamine I at concentrations of 1 μm, 2 μm, 4 μm and 8 μm on *Pseudomonas aeruginosa* PAO1 in the respective 14-ml polystyrene tubes. As solvent controls, *Pseudomonas aeruginosa* strain PAO1 was grown in LB medium ("LB"), and in LB and methanol ("MeOH") in another tube. As shown in FIG. 1B, the growth of the bacterial culture in each respective polystyrene tube is measured as optical density at 600 nm. As shown in FIG. 1C, the growth of biofilm in each respective polystyrene tube was measured as optical density at 570 nm.

FIG. 2 shows the influence of zeamine I on dispersing biofilm by *Pseudomonas aeruginosa* PAO1. FIG. 2A shows the influence of zeamine I at concentrations of 15 μm and 20 μm on *Pseudomonas aeruginosa* PAO1. As solvent controls, *Pseudomonas aeruginosa* strain PAO1 was grown in LB medium ("LB") in one tube and in LB and methanol ("MeOH") in another tube. The growth of the biofilms in each polystyrene tube was measured as optical density at 570 nm (FIG. 2B) and 600 nm (FIG. 2C) respectively.

EXAMPLES

Example 1

Culture Conditions and Isolation of Zeamine I.

*Dickeya zeae* strain DZ1 (isolated from rice), which produce bactericidal compound(s) when assayed against *E. coli* DH5α, was used. *D. zeae* strain was grown at 28° C. on yeast extract broth (YEB) agar, which contained (per liter) 10 g Bacto tryptone, 5 g yeast extract, 5 g sucrose, 5 g NaCl, 15 g agar and 1 mM $MgSO_4.7H_2O$ (pH 7.0) for 24 h. Single colonies were used to inoculate YEB broth (50 ml in a 250 ml conical flask) and incubated at 28° C. (200 rpm) for overnight to prepare start culture. The minimal medium ($K_2HPO_4$ 10.5 g/l, $KH_2PO_4$ 4.5 g/l, $(NH_4)_2SO_4$ 2 g/l, mannitol 2 g/l, glycerol 2 g/l, $MgSO_4.7H_2O$ 0.2 g/l, $FeSO_4$ 5 mg/l, $CaCl_2$ 10 mg/l and $MnCl_2$ 2 mg/l; pH 7.0) was inoculated with start culture (0.2% v/v) and grown at 28° C., 120 rpm for 24 h. Cells were removed by centrifugation at 13,000 rpm, 15° C. for 15 min. The supernatant was adjusted to pH 10 with 5 M NaOH. After basification, the supernatant was concentrated by 10 folders by rotary evaporation and extracted twice by 3 volumes of organic solvent (n-butanol:ethyl acetate=2:1). The extract was subjected to gel filtration chromatography (GFC) on Sephadex LH-20 after removal of organic solvent by rotary evaporation. MeOH was used to elute GFC. Fractions with antibiotic activity were combined following bioassay. Further purification was carried out by gradient HPLC on C18 reverse phase column eluted with MeOH in $H_2O$ (0-5 min 5%, 5-50 min 5%-75%, 50-51 min 75%-95%, 51-55 min 95%, 55-56 min 95%-5% and 56-60 min 5%). The major active fraction with the retention time at 31.0 min (zeamine I) and a minor active fraction at 29.4 min (zeamine II) were used for structural analysis.

Antibiotic Bioassay.

The bactericidal activity was assayed using *Escherichia coli* strain DH5α following the method described previously by Zhang et al. (Zhang et al. (1998). Factors affecting biosynthesis by *Xanthomonas albilineans* of albicidin antibiotics and phytotoxins. J. Appl. Microbiol. 85: 1023-1028). Briefly, an overnight LB culture of strain DH5α was diluted by 10-fold in sterilized water, and 100 microliters of the dilute were added to 5 ml of 1% agarose solution, which was autoclaved with temperature being maintained at 50° C. The bioassay plate was prepared by adding the mixture onto a plate containing 20 ml LB agar. Bioassay was conducted by adding 20 microliters of bacterial supernatants or fractions to the 4-mm diameter wells in bioassay plate. The plate was incubated at 37° C. overnight before examination of inhibition zone.

Determination of Minimum Inhibition Concentration (MIC).

The minimum inhibition concentration (MIC) of zeamine I was carried out according to the NCCLS guidelines (4).

Briefly, 96-well plates containing 2-fold serial dilutions of zeamine I and control antibiotics were prepared with LB liquid medium. The fresh overnight LB cultures of tested bacterial strains were then inoculated to the above plates after dilution to yield a final density of $10^6$ CFU/ml and $10^7$ CFU/ml, respectively. The plates were then incubated with gentle shaking at 30° C. or 37° C. depending on the preferred growth temperature of the tested strains. After 24 h, the plates were collected to measure $OD_{600}$. The MIC was defined as the lowest concentration of the antibiotic allowing no visible growth. The MIC assay was repeated twice each time with triplicate.

Purification of Antimicrobial Compounds.

Strain DZ1 produced significantly higher amount of antimicrobial compound(s) in the minimum medium than in LB medium. In large scale purification, about 30 liters of DZ1 cultures grown in minimum medium were collected. The supernatants were subjected solvent extraction, gel filtration chromatography on Sephadex LH-20, and gradient HPLC on a C18 reverse phase column. The major active fraction (zeamine I) with the retention time at 31.0 min and a minor active fraction (zeamine II) at 29.4 min were subjected to structural analysis.

Structural Analysis.

Zeamine II, which represents less than 40% (solid weight) of the total antimicrobial compounds, was isolated as a colorless solid. Accurate ESIMS revealed a molecular formula of $C_{40}H_{88}ON_5$, [M+H]/e, 654.6993, (cal. 654.6983); MS data supported a saturated structure without any rings or double bonds. In normal ESI analysis, there were the peaks: 655, 638, 621, 604, 587 and 569, which represented M+H, M+H—$NH_3$, M+H-$2NH_3$, M+H-$3NH_3$, M+H-$4NH_3$ and M+H-$4NH_3$-$H_2O$. Those fragments suggested that there were four secondary amino groups and one secondary hydroxyl group in the skeleton. $^1$H and $^{13}$C spectra revealed the existence of a primary amino group. C—C bond cleavage in EI analysis was employed to identify the positions of those amino groups. In EI analysis, there were peaks at 638, 592, 566, 464, 438, 337, 331, 227 and 100.

Zeamine I (Formula II), a colorless solid, presents as a major (more than 60%, solid weight) antimicrobial component of the total antimicrobial compounds. Accurate ESIMS revealed a molecular formula of $C_{49}H_{105}O_4N_6$, [M+H]/e, 841.8218, (cal. 841.8192). In ESI analysis, besides the peak of 842, there were the peaks: 655, 638, 621, 604, 587 and 569, which represented M+H, M+H—$NH_3$, M+H-$2NH_3$, M+H-$3NH_3$, M+H-$4NH_3$ and M+H-$4NH_3$—$H_2O$ in the analysis of zeamine I. These data showed that zeamine I could be a hydrolyzed product or precursor of zeamine II. In EI analysis, this hydrolyzed component showed peaks at 638, 592, 566, 464, 438, 337, 331, 227 and 100; which agrees well with the forty-carbon side chain as shown below.

putative hydrolyzed component or precursor (zeamine II). In $^{13}$C spectra, there was a signal at $\delta_C$ 174 ppm. This suggested an extra carbonyl group of an amide compared with zeamine II. Three extra methine carbons locate between 60 and 70 ppm. COSY spectra revealed the key correlations among protons in fragment (from C-1' to C-9'). Both of the two oxymethine protons at $\delta_H$ 4.24 ppm (3'-H) and $\delta_H$ 4.04 ppm (5'-H) showed correlations with methylene protons at $\delta_H$ 1.73 ppm (4'-H). 3'-H also showed correlation with methylene protons at $\delta_H$ 2.41 ppm (2H, 2'-H). There was also another correlation from 5'-H to methine proton at $\delta_H$ 2.90 ppm (6'-H). There were correlations between the two doublet methyl groups ($\delta_H$ 1.09 ppm and $\delta_H$ 1.04 ppm) and methine proton at $\delta_H$ 2.05 ppm (7'-H); and this methine proton showed correlation with 6'-H. HMBC correlations from H-2' to carbonyl carbon at $\delta_C$ 174.0 ppm (C-1') and from H-8' to C-6' ($\delta_C$ 62.1 ppm), C-7' ($\delta_C$ 26.2 ppm) and C-9' ($\delta_C$ 18.1 ppm) confirmed the structure (Formula II).

Zeamine I is a Polyketide.

Based on the findings that addition of extra glycerol to the culture medium increased the yield of zeamines and their structures share similarities to polyketides, we postulated that some fragments in the structures of zeamine I might be synthesized by polyketide synthase (PKS). This hypothesis was confirmed by $^{13}$C-labeling experiments (Table 1). Addition of sodium [2-$^{13}$C]acetate enriched the $^{13}$C isotope at C-1, C-4, C-2', C-4' and other even number carbons except C-5' to C-9'. Enrichment at C-2, C-3, C-1', C-3' and other odd number carbons except C-5' to C-9' was observed in sodium [1-$^{13}$C] acetate feeding experiment. Thus, the amino isobutyl moiety, formed by C-5' to C-9', is not synthesized by PKS and may come from amino acids such as valine. [1,2-$^{13}$C]acetate was used in a further feeding experiment to determine the distribution of acetate units (Table 2). The data suggest that in zeamine I, except the amino isobutyl moiety, the other forty four carbons are derived from twenty two acetate units.

Zeamine I is a Potent Antibiotic.

The minimum inhibition concentration (MIC) of zeamine I was determined on a range of bacterial pathogens. The results showed that zeamine I was a highly potent antibiotic on both Gram-negative and Gram-positive bacterial pathogens, with MIC at a level less than 20 μg/ml (Table 3). In contrast, a high dosage of ampicillin, which is a commonly used antibiotic, was required to inhibit the growth of these bacterial pathogens.

NMR data: $^1$H NMR of zeamine I (MeOH-$d_4$, 400 MHz): δ=0.95 (t, J=6.6 Hz, 3H, 40-$H_3$), 1.04 (d, J=6.8 Hz, 3H, 9'-$H_3$), 1.09 (d, J=6.8 Hz, 3H, 8'-$H_3$), 1.73 (m, 2H, 4'-$H_2$), 2.05 (m, 1H, 7'-H), 2.41 (m, 2H, 2'-$H_2$), 2.90 (m, 1H, 6'-H),

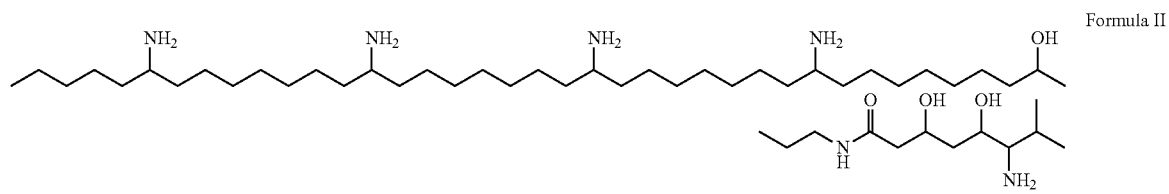

Formula II

Its structure was further established by elucidation of 1D and 2D NMR spectra. $^1$H spectra of zeamine I showed two oxymethine protons, four methylene protons, two methine protons and two doublet methyl groups compared with the 3.17 (m, 4H, 11-H, 19-H, 27-H and 35-H), 3.30 (m, 1H, 1-H), 3.59, (m, 1H, 3-H), 4.04 (m, 1H, 5'-H), 4.24 (m, 1H, 3'-H); other protons crowed from 1.5 ppm to 1.7 ppm and from 1.3 ppm to 1.5 ppm.

TABLE 1

$^{13}$C enrichment in zeamine I after feeding [1-$^{13}$C] and [2-$^{13}$C] acetate

| C no. | $\delta_C$ | [1-$^{13}$C]* | [2-$^{13}$C]** |
|---|---|---|---|
| 1 | 37.7 | 5 | |
| 2 | 38.6 | | 4 |
| 3 | 70.3 | 5 | |
| 4 | 38.0 | | 4 |
| 5 | 25.9 | 4 | |
| 6 | 30.4 | | 4 |
| 7 | 30.4 | 4 | |
| 8 | 30.6$^c$ | | 4 |
| 9 | 26.3$^b$ | 6 | |
| 10 | 34.0$^a$ | | 4 |
| 11 | 53.1 | 3 | |
| 12 | 34.0$^a$ | | 5 |
| 13 | 26.3$^b$ | 6 | |
| 14 | 30.6$^c$ | | 4 |
| 15 | 30.6$^c$ | 4 | |
| 16 | 30.6$^c$ | | 4 |
| 17 | 26.3$^b$ | 6 | |
| 18 | 34.0$^a$ | | 4 |
| 19 | 53.1 | 3 | |
| 20 | 34.0$^a$ | | 5 |
| 21 | 26.3$^b$ | 6 | |
| 22 | 30.6$^c$ | | 4 |
| 23 | 30.6$^c$ | 4 | |
| 24 | 30.6$^c$ | | 4 |
| 25 | 26.3$^b$ | 6 | |
| 26 | 34.0$^a$ | | 5 |
| 27 | 53.1 | 3 | |
| 28 | 33.9$^a$ | | 5 |
| 29 | 26.3$^b$ | 6 | |
| 30 | 30.6$^c$ | | 4 |
| 31 | 30.6$^c$ | 4 | |
| 32 | 30.6$^c$ | | 4 |
| 33 | 26.3$^b$ | 6 | |
| 34 | 33.8$^a$ | | 5 |
| 35 | 53.1 | 3 | |
| 36 | 32.8 | | 4 |
| 37 | 26.8 | 4 | |
| 38 | 30.8 | | 2 |
| 39 | 23.6 | 5 | |
| 40 | 14.4 | | 3 |

| C no. | $\delta_C$ | [1-$^{13}$C] | [2-$^{13}$C] |
|---|---|---|---|
| 1' | 174.0 | 5 | |
| 2' | 44.6 | | 3 |
| 3' | 67.5 | 5 | |
| 4' | 42.0 | | 3 |
| 5' | 67.7 | | |
| 6' | 62.1 | | |
| 7' | 26.2 | | |
| 8' | 18.1 | | |
| 9' | 19.8 | | |

$^{a,b,c}$are exchangeable each other.
*,**Because of serious overlapping of signals, the data are estimated by measuring spectra.
Measured in methanol-d$_4$ on Bruker DRX400

TABLE 2

$^1J_{CC}$ value (Hz) of zeamine I after feeding [1,2-$^{13}$C] acetate

| $^1J_{CC}$ | |
|---|---|
| $^1J_{C1C2}$ | 38.0 |
| $^1J_{C3C4}$ | 38.0 |
| $^1J_{C5C6}$ | 36.4 |
| $^1J_{C7C8}$ | 34.5 |
| $^1J_{C9C10}$ | 34.6 |
| $^1J_{C11C12}$ | 35.9 |
| $^1J_{C13C14}$ | 34.4 |
| $^1J_{C15C16}$ | 34.5 |
| $^1J_{C17C18}$ | 34.8 |
| $^1J_{C19C20}$ | 35.9 |

TABLE 2-continued $^1J_{CC}$ value (Hz) of zeamine I after feeding [1,2-$^{13}$C] acetate

| $^1J_{CC}$ | |
|---|---|
| $^1J_{C1'C2'}$ | 49.2 |
| $^1J_{C21C22}$ | 34.4 |
| $^1J_{C23C24}$ | 34.5 |
| $^1J_{C25C26}$ | 34.8 |
| $^1J_{C27C28}$ | 35.9 |
| $^1J_{C29C30}$ | 34.8 |
| $^1J_{C31C32}$ | 34.5 |
| $^1J_{C33C34}$ | 34.8 |
| $^1J_{C35C36}$ | 35.9 |
| $^1J_{C37C38}$ | 34.8 |
| $^1J_{C39C40}$ | 34.5 |
| $^1J_{C3'C4'}$ | 38.8 |

Measured on Bruker DRX400

TABLE 3

MIC of Zeamine I on various bacterial strains*

| Strain | Zeamine I (µg/ml) | Ampicillin (µg/ml) | Kanamycin (µg/ml) | Tetracycline (µg/ml) |
|---|---|---|---|---|
| Staphylococcus aureus ATCC 25531 | 0.3 | 15.6 | 6.2 | 3.1 |
| Staphylococcus aureus BBA-41 | 0.3 | >500 | 12.5 | 6.2 |
| Bacillus cereus XJ8 | 3.1 | 100 | 3.1 | 6.2 |
| Pseudomonas aeruginosa PAO1 | 5.0 | 400 | 200 | 25.0 |
| Pseudomonas aeruginosa PA14 | 6.2 | 800 | 200 | 12.5 |
| Burkholderia cepacia H111 | 50 | >800 | 6.2 | 12.5 |
| Burkholderia cepacia J2315 | 25 | >800 | 400 | 50 |
| Enterobacter aerogenes ATCC 13048 | 3.1 | >800 | 3.1 | 3.1 |
| Klebsiella pneumonia | 6.2 | >800 | 3.1 | 6.2 |
| Salmonella enterica | 3.1 | 12.5 | 12.5 | 25 |
| E. coli CFT073 | 3.1 | 25 | 6.2 | 0.75 |
| E. coli DH5α | 0.5 | 25.0 | 10.0 | 3.1 |
| Aeromonas hydrophila | 10.0 | 125.0 | 25.0 | 6.2 |
| Mycobacterium smegmatis | 3.0 | | | |

*For determination of MIC, overnight bacterial culture was diluted to a final population density of 1 × 10$^6$ CFU/ml in LB medium containing corresponding antibiotic as indicated. The culture was incubated at 30° C. with shaking at 250 rpm for 24 h prior to measurement of growth.

Example 2

Influence of Zeamine I on Biofilm Formation by *Pseudomonas aeruginosa* PAO1

The effect of zeamine I on biofilm formation by *Pseudomonas aeruginosa* was tested using two approaches. First, the *P. aeruginosa* strain PAO1 overnight cultures were diluted in fresh LB medium to a final colony forming units (CFU) of about 2×10$^7$. The diluted cultures (2 ml) were transferred to a 14-ml polystyrene tube (17×100 mm; FALCON, 352057), to which Zeamine I was added at a final concentration of 1 µm, 2 µm, 4 µm, and 8 µm, respectively. The bacterial cultures were incubated at 37° C. with shaking at 250 rpm for a period as stated in FIG. 1. Bacterial suspensions (planktonic cells) were carefully removed for measurement of OD$_{600}$. The bacterial cells bound to the wall of the tubes (biofilms) were stained with 0.1% crystal violet (Sigma) for 15 min at room temperature and the tubes were then rinsed several times with water. The tubes were air-dried at room temperature and then photographed. For quantification, the attached cells (biofilms) were suspended in 3 ml of 75% ethanol. The absorbance at 570 nm was measured with a spectrophotometer. Each experiment was repeated at least three times.

The results showed that at a final concentration of 2 μM and above, zeamine I inhibited biofilm formation and bacterial growth (FIGS. 1A, 1B, 1C). In contrast, the pathogen formed biofilms when grown in LB medium (LB) and the same medium containing 10 μl of methanol as solvent control.

Example 3

Influence of Zeamine I on Dispersing Biofilm by *Pseudomonas aeruginosa* PAO1

The effect of zeamine I was tested in dispersing biofilm. Under the same conditions as described in Example 1, *P. aeruginosa* strain PAO1 were grown for 5 h, when biofilm formation had been established (FIG. 1A, FIG. 1C), before addition of zeamine I at a final concentration of 15 and 20 μM, respectively. After incubation for 18 h under the same conditions, bacterial cell density and biofilm were measured.

Figure 2:
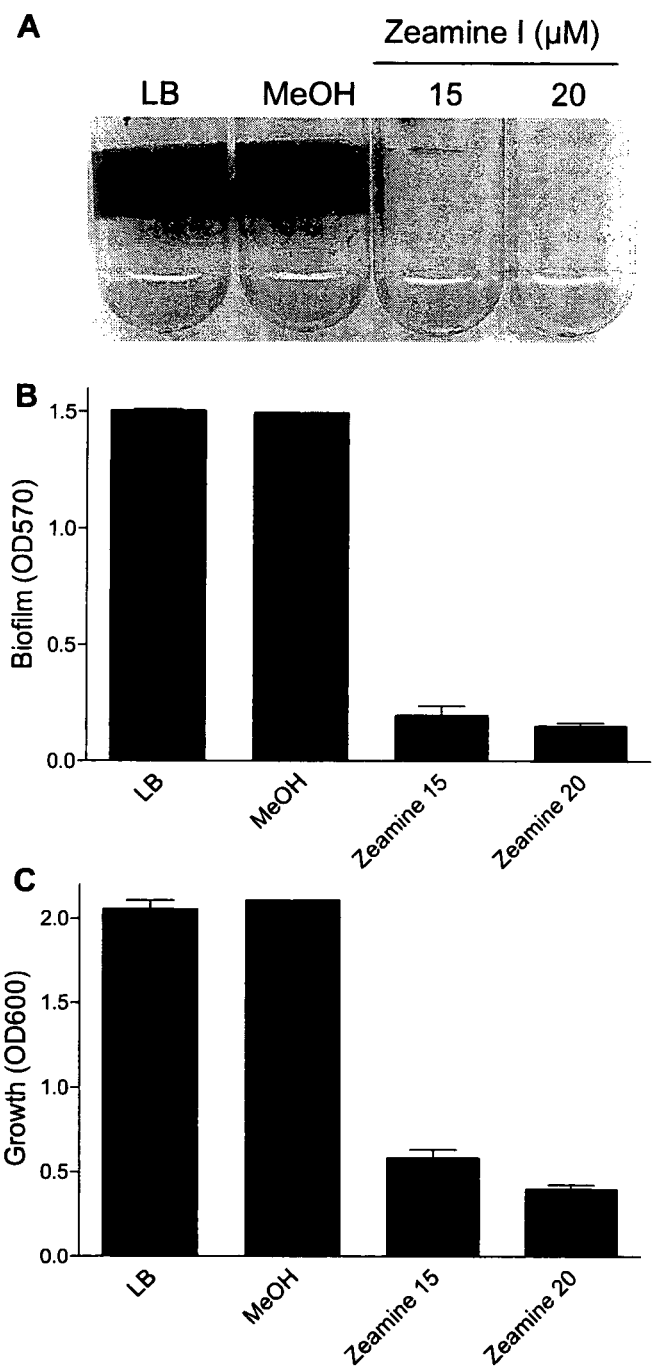

The results showed that zeamine I treatment had basically eliminated the biofilms from the wall of tube (FIG. 2A). Quantitative analysis indicated that zeamine I treatment reduced biofilms by over 85% (FIG. 2B). Similarly, bacterial growth had also been significantly reduced (FIG. 2C).

We claim:

1. A compound of formula I

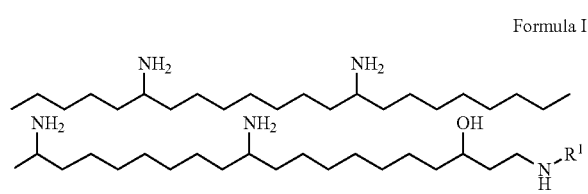

Formula I wherein

R$^1$ is unsubstituted or substituted C$_1$-C$_{10}$ alkyl, unsubstituted or substituted C$_2$-C$_{10}$ alkenyl, unsubstituted or substituted C$_2$-C$_{10}$ alkynyl, unsubstituted or substituted C$_3$-C$_8$ cycloalkyl, unsubstituted or substituted C$_1$-C$_{10}$ alkoxy, unsubstituted or substituted C$_3$-C$_8$ cycloalkoxy, unsubstituted or substituted C$_6$-C$_{14}$ aryl, an unsubstituted or substituted 5- to 10-membered heteroaryl wherein 1 to 4 ring atoms are independently selected from nitrogen, oxygen and sulfur, an unsubstituted or substituted 5- to 10-membered heteroalicyclic ring wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, and —S(O)$_2$NRR', R and R' are independently selected from the group consisting of hydrogen and unsubstituted or substituted C$_1$-C$_{10}$ alkyl, unsubstituted or substituted C$_2$-C$_{10}$ alkenyl, unsubstituted or substituted C$_2$-C$_{10}$ alkynyl;

or a tautomer, geometrical isomer, enantiomer, diastereomer, racemate form, pharmaceutically acceptable salt or prodrug thereof.

2. The compound of claim 1, wherein R$^1$ is —C(O)R and R is unsubstituted or substituted C$_1$-C$_{10}$ alkyl.

3. The compound of claim 2, wherein R is substituted heptanyl.

4. The compound of claim 3, wherein R is 3-amino-4,6-dihydroxy-2-methyl-heptan-7-yl.

5. The compound according to claim 1, wherein the compound is a compound of formula II

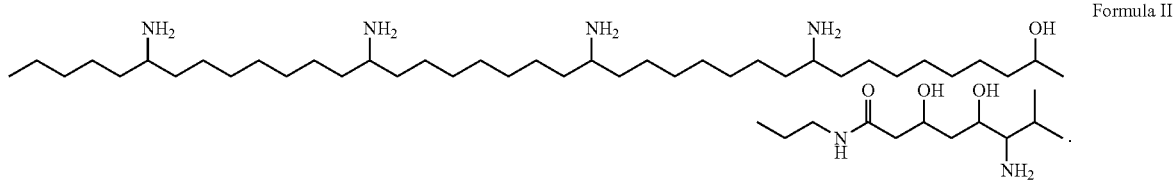

Formula II

6. A composition comprising the compound of claim 1.

7. The composition of claim 6, wherein the composition is a personal hygiene article, a toiletry or a cosmetic.

8. The composition of claim 7, wherein the toiletry is an oral hygiene product.

9. The composition of claim 6, wherein the composition is a pharmaceutical composition.

10. The composition of claim 9, further comprising a pharmaceutically acceptable carrier.

11. A method for the treatment or prevention of a bacterial infection in a subject comprising administering a therapeutically effective amount of the compound of claim 1 to a subject in need thereof.

12. The method according to claim 11, wherein the bacterial infection is a *Acinetobacter, Actinomyces, Aeromonas, Bordetella, Borrelia, Brucella, Burkholderia, Campylobacter, Chlamydia, Clostridium, Corynebacterium, Enterococcus, Erwinia, Escherichia, Francisella, Haemophilus, Helicobacter, Klebsiella, Legionella, Leptospira, Listeria, Mycobacterium, Mycoplasma, Neisseria, Pseudomonas, Rickettsia, Salmonella, Shigella, Staphylococcus, Streptococccus, Treponema, Verllonella, Vibrio* or *Yersinia* infection.

13. The method according to claim 12, wherein the bacterial infection is a *Staphylococcus aureus, Mycobacterium smegmatic, Pseudomonas aeruginosa, Burkholderia cepacia, Klebsiella pneumoniae, Aeromonas hydrophila, Erwinia carotovora, Erwinia chrysanthemi,* or *Escherichia coli* infection.

14. A method for producing a compound according to claim 1 comprising
   (a) cultivating an organism of the genus *Dickeya*; and
   (b) isolating said compound from said organism.

15. The method of claim 14, wherein the organism of the genus *Dickeya* is *Dickeya zeae*.

16. The method according to claim 14, wherein the cultivating step comprises incubation of *Dickeya zeae* in a medium comprising glycerol.

17. The compound of Formula I according to claim 1, obtained by isolation from an organism of the genus *Dickeya*.

18. A method for the treatment or prevention of a bacterial infection in a subject comprising administering a therapeutically effective amount of the composition of claim 6 to a subject in need thereof.

\* \* \* \* \*

UNITED STATES PATENT AND TRADEMARK OFFICE
CERTIFICATE OF CORRECTION

PATENT NO. : 8,748,661 B2  
APPLICATION NO. : 13/128220  
DATED : June 10, 2014  
INVENTOR(S) : Jinling Xu et al.

Page 1 of 1

It is certified that error appears in the above-identified patent and that said Letters Patent is hereby corrected as shown below:

Title Page  
Item (75), Inventors:  
"Jinling Xu, Singapore (SG); Lianhui Zhang, legal representative, Singappore (SG); Jien Wu, Singapore (SG); Haibao Zhang, Singapore (SG)" should read --Jinling Xu, Singapore (SG), Deceased; Lianhui Zhang, Singapore (SG), Legal Representative; Lianhui Zhang, Singapore (SG); Jien Wu, Singapore (SG); Haibao Zhang, Singapore (SG)--.

Signed and Sealed this  
Twenty-second Day of March, 2016

Michelle K. Lee  
*Director of the United States Patent and Trademark Office*